United States Patent [19]

Stephan et al.

[11] Patent Number: 4,540,820

[45] Date of Patent: Sep. 10, 1985

[54] PRODUCTION OF ANIMAL FEED GRADE BIURET

[75] Inventors: Kurt F. Stephan, Wenatchee; John T. Stephan, East Wenatchee, both of Wash.

[73] Assignee: Moorman Manufacturing Company, Quincy, Ill.

[21] Appl. No.: 455,326

[22] Filed: Jan. 3, 1983

Related U.S. Application Data

[63] Continuation-in-part of Ser. No. 265,550, May 20, 1981, , which is a continuation-in-part of Ser. No. 178,132, Aug. 15, 1980, abandoned.

[51] Int. Cl.$^3$ ............................................. C07C 127/24
[52] U.S. Cl. ............................................. 564/38; 426/69
[58] Field of Search ............................................. 564/38

[56] References Cited

U.S. PATENT DOCUMENTS

| | | | |
|---|---|---|---|
| 2,145,392 | 1/1939 | Harmon | 260/553 |
| 2,370,065 | 2/1945 | Olin | 260/553 |
| 2,524,049 | 10/1950 | Garbo | 260/553 |
| 2,768,895 | 10/1956 | Kamlet | 99/2 |
| 2,861,886 | 11/1958 | Colby | 99/2 |
| 2,918,467 | 4/1956 | Hibbits et al. | 260/249.7 |
| 3,057,918 | 10/1962 | Formaini et al. | 260/553 |
| 3,093,641 | 6/1963 | Formaini | 260/248 |
| 3,150,177 | 9/1964 | Kluge | 260/553 |
| 3,453,098 | 7/1969 | Kamlet | 71/30 |
| 3,928,438 | 12/1975 | Beale, Jr. et al. | 260/553 B |
| 3,935,260 | 1/1976 | Schlosser | 260/553 B |
| 3,946,073 | 3/1976 | Cook, Jr. | 260/553 B |
| 4,055,598 | 10/1977 | Lee | 260/553 B |

FOREIGN PATENT DOCUMENTS

| | | |
|---|---|---|
| 1068693 | 12/1955 | Fed. Rep. of Germany . |
| 47-41888 | 4/1972 | Japan . |
| 95513 | 10/1960 | Netherlands . |
| 830114 | 6/1957 | United Kingdom . |
| 1155907 | 5/1968 | United Kingdom . |

*Primary Examiner*—Charles F. Warren
*Assistant Examiner*—Robert A. Picard
*Attorney, Agent, or Firm*—Graybeal & Cullom

[57] ABSTRACT

Preparation of a composition particularly suitable for use as feedstock in the production of animal feed grade biuret by solid state pyrolyzation thereof in a recirculating oven, which composition comprises from about 37% to about 25% urea, from about 45% to about 60% biuret, and from about 3% to about 20% cyanuric acid, by weight, such preparation involving sparging air or other non-reactive gas through a urea charge at a temperature of from about 145° C. to about 165° C. and at a rate of between about two to about ten cu. ft. of gas/hr/lb of urea for a period of at least four hours, then cooling and comminuting the product.

8 Claims, No Drawings

PRODUCTION OF ANIMAL FEED GRADE BIURET

CROSS REFERENCE TO RELATED APPLICATION

This application is a continuation-in-part of our pending application Ser. No. 265,550, entitled Biuret Production by Controlled Pyrolysis of Urea, and filed May 20, 1981, which is in turn a continuation-in-part of our now abandoned application Ser. No. 178,132, entitled Production of Biuret By The Controlled Pyrolysis of Urea, and filed Aug. 15, 1980.

BACKGROUND OF THE INVENTION

1. Field of the Invention

The present invention relates to the production of a partially pyrolyzed urea composition particularly suitable for use as the feedstock for the production of animal feed grade biuret, and containing controlled amounts of biuret, cyanuric acid, triuret, and other homologs. Production of such composition involves the controlled pyrolysis of urea at elevated temperatures above the melting point of urea and at a pressure above atmospheric while subjected to sparged air or other non-reactive gas at the rate of about two to about ten cubic feet of gas per hour pound of urea, and cooling and comminuting the resulting product.

2. Description of the Prior Art

Harmon U.S. Pat. No. 2,145,392 discloses a basic process for pyrolysis of urea wherein urea is heated in the temperature range of 130°–205° C. while under partial vacuum in the absence of any catalyst to produce principally biuret, cyanuric acid, and other related compounds. Biuret is a useful chemical compound having considerable utility in prepared feeds for ruminant animals. Crude technical mixtures of urea, biuret, triuret, and cyanuric acid have long been used as cattle feed supplements. The United States Department of Agriculture, Food and Drug Administration has approved pyrolyzed urea compositions having not more than 15% urea, not less than 55% biuret, and not more than 30% of the sum of cyanuric acid, triuret, or other related compounds, and not more than 0.5% of oil, by weight, as a cattle feed additive.

Garbo U.S. Pat. No. 2,525,049 discloses much the same process for producing biuret from urea as is disclosed by Harmon U.S. Pat. No. 2,145,392, with the added feature of accelerating the reaction by the use of one or more catalysts and in some instances use also of a hydrocarbon fluidizing medium such as naphthalene or kerosene.

Olin U.S. Pat. No., 2,370,065 presents another teaching of use of an entraining agent such as toluene or naphtha to aid in the removal of ammonia when pyrolyzing urea to produce biuret.

Kluge U.S. Pat. No. 3,150,177 presents a biuret production process similar to that disclosed by Harmon U.S. Pat. No. 2,145,392 coupled with the use of disodium phosphate or boric acid as a catalyst.

Kamlet U.S. Pat. No. 2,768,895 presents a rather omnibus disclosure of use of biuret rich urea condensation products as animal feed. Kamlet U.S. Pat. No. 3,453,098 presents a variation of the process wherein biuret rich urea autocondensation products are dissolved in boiling water and then cooled to recrystallize the biuret products, which are then said to contain not less than 95% biuret and be characterized by complete removal of ammonium cyanate, the product thus being rendered suitable for use as a depot fertilizer without the phytotoxic consequences said to be characteristic of such a product when substantial ammonium cyanate is present.

Colby et al, U.S. Pat. No. 2,861,886 presents another early disclosure of use of biuret rich compositions used as constituent ingredients of animal feed supplements.

Great Britain Pat. No. 1,155,907 discloses the pyrolysis of urea to product a biuret rich reaction product, including the separation of a urea containing mixture from the reaction product, and recycling of the separated urea containing mixture to the reactor as a continuous process.

Japan Patent Publication No. 47-41888 (1972) discloses the production of purified biuret. The English language abstract published with Japan Patent Publication No. 47-41888 states that this publication discloses a process for preparing purified biuret by treating urea decomposition products with hot water, filtering the obtained mixture, treating the filtrate with aqueous ammonia and cooling it to below 40° C., separating the precipitated biuret, recovering ammonia from the supernatant liquor by evaporating water, and recycling residual urea after decomposing it by heating. Substantially pure biuret (separated from cyanuric acid and triuret) is obtained. Such abstract continues to give the following example. 100 grams urea is decomposed at 150° C. while introducing 22.0 l./min. air for 2 hours to give 38.8 grams biuret, 4.0 grams cyanuric aid, 3.8 grams triuret and 44.0 grams unreacted urea. The products are partly dissolved in 150 ml. water at 70° C. The mixture is filtered and the filtrate is treated with 5 grams $NH_3$ and cooled to 40° C. The precipitate (24.1 grams; yield 98.8%) is biuret containing 1.2% urea and only traces of cyanuric acid and triuret.

Formaini et al in U.S. Pat. No. 3,057,918 proposes a continuous process for the production of biuret wherein new urea plus recycled previously pyrolyzed urea is sparged with air while molten at elevated temperature to produce a feedstock for a pressure digestion step whereby a relatively pure biuret is separated from the mother liquor of the ammonia digestion step by a controlled vacuum crystallization and the unwanted by-product is evaporated to give the solid recycle material added along with urea to make the feedstock for the initial pyrolysis step. The urea content of the typical feedstock entering the ammonia digestion step has the following analysis:

| Biuret | 28–42% |
|---|---|
| Urea | 65–40% |
| Cyanuric Acid | 3–14% |
| Triuret | 5–7% |

This is to be contrasted with the typical analysis for the feedstock of the present invention which is:

| Biuret | 45–60% |
|---|---|
| Urea | 37–25% |
| Cyanuric Acid | 3–20% |
| Triuret | 3–10% |

The pyrolysis of urea to produce biuret, triuret, cyanuric acid, ammelide, melamine and other homologs, is well known. When urea is pyrolyzed ammonia is always an accompanying byproduct. It was early established by Harmon in U.S. Pat. No. 2,145,392 that the pyrolysis of urea to produce biuret was aided by the application of controlled vacuum whereby the byproduct ammonia was effectively removed from the reactor thus lowering the partial pressure of ammonia and thereby driving the pyrolysis reaction toward higher biuret content. The use of volatile entraining agents such as toluene to sweep out byproduct ammonia in biuret manufacture was early suggested by Olin in U.S. Pat. No. 2,370,065. The use of gases such as nitrogen or air to sweep out byproduct ammonia formed during urea pyrolysis is suggested in U.S. Pat. No. 2,918,467 by Hibbitts et al in the production of a pyrolyzed urea feedstock used in the production of melamine. Formaini U.S. Pat. No. 3,093,941 uses air as the stripping gas to remove byproduct ammonia formed during urea pyrolysis in the production of a pyrolyzed urea feedstock used in the production of cyanuric acid. Formaini U.S. Pat. No. 3,057,918 uses air as the stripping gas to remove byproduct ammonia formed during continuous urea pyrolysis in the production of a pyrolyzed urea feedstock used in an extraction process to produce substantially pure biuret.

SUMMARY OF THE INVENTION

In the present invention air or like nonreactive gas is used as the stripping gas to remove byproduct ammonia formed during urea pyrolysis to produce a feedstock having a controlled fusion point which is attained by controlling the analysis of the feedstock in regard to the urea, biuret, triuret, and cyanuric acid content. A suitable feedstock product for use in the process claimed in our copending U.S. patent application Ser. No. 265,550 is one that has the following characteristics:

| Chemical Analysis | |
| --- | --- |
| % Urea | 37-25% |
| % Biuret | 45-60% |
| % Cyanuric Acid | 3-20% |
| % Triuret | 3-10% |
| Melting Point 110-130° C. | |

Feed grade biuret is a mixture of nitrogen containing chemicals produced by the pyrolysis of urea. The Food and Drug Administration of the U.S. Department of Agriculture has promulgated a specification for feed grade biuret (see Code of Federal Regulations, Title 21, Section 573,220), as follows:

| | |
| --- | --- |
| Minimum biuret content | 55% |
| Maximum urea content | 15% |
| Maximum cyanuric acid, triuret, tetrauret, and others | 30% |
| Maximum oil content | 0.5% |

In the two-stage process described in our aforesaid application Ser. No. 265,550 partially pyrolyzed urea containing not over 25% cyanuric acid and more than 20% urea by weight is converted to animal feed grade biuret by subjecting the partially pyrolyzed urea feedstock in particulate form to a mild heat treatment in the substantially solid state with forced air flow through the particulate reaction mass. A product results having a high concentration of biuret and a product with a minimum of 55% biuret, a maximum of 15% urea, and a maximum of 30% cyanuric acid and similar urea pyrolysis by-products is easily produced. Such product is hydrocarbon-free and eminently suitable as a feed additive for cattle and needs no additional separation step to remove excess urea and cyanuric acid. In such process a feedstock consisting of partially pyrolyzed urea in dry particulate form and containing not over about 25% cyanuric acid is treated in an oven with forced air recirculation at a temperature at or slightly below the softening point of particles, e.g. at a temperature between about 100° C. and about 140° C., and preferably between 115° C. and 125° C. for a period of time of generally between about 15 hours to about 200 hours and preferably from about 24 hours to 180 hours. During this stage of pyrolyzation it is essential that the feedstock be in an essentially solid state with at most only incipient surface fusion of particles, as distinguished from the molten, i.e. liquid state so that substantially sublimation can occur as well as evolution of ammonia from the product.

The ground feedstock is suitably placed in trays or the like to a bed depth of between ½ inch and 3 feet or more, and placed in a forced air circulating oven or the like with hot air circulated through the particulate mass in each tray, preferably upwardly through each tray. The temperature is preferably thermostatically controlled to within ±3° C. within the oven.

The comminuted feestock is placed in or on a container porous to air, such as a tray or other box-type container with a screen or like foraminous bottom and open top, which arrangements provide what may be generically termed a fixed bed. Alternatively, the feedstock bed may be arranged on a wire screen or like foraminous conveyor, or in a fluidizing chamber, which arrangements provide what may be generically termed a movable bed.

The depth of the bed of the particulate material can be any desired depth consistent with the need to maintain substantially and continuing forced air flow in contact with the material surfaces, and considering also that under a given operating condition a given total amount of contact of moving air with the surfaces of the particles is necessary to achieve the result of substantial urea sublimation and urea conversion to biuret, which considerations involve several interrelated factors such as average mesh size of the particles, the temperature of the air, the depth of the particle bed and the volume of air flow past the particles. Thus, for example, in a situation where a fixed bed, 2 feet in depth, is composed of particles having an average mesh size of 8 mesh, a pressure drop of 0.16 psig per foot of bed has been found satisfactory for the operating condition where the air and particles are heated to a temperature of 127° C. and for 36 hours. Correspondingly, however, when the average particle size is 4 mesh, an optimized pressure drop through a bed 2 feet thick to accomplish a similar end product at the same temperature has been found to be 0.13 psig per foot of bed, and the heating should continue for a period of 50 hours.

Comminution of the solidified and broken up pieces of the partially pyrolyzed reaction product resulting from the first stage of reaction of urea and the addition thereto of feed grade biuret powder to increase the melting point and expedite cooling of the reaction product, can be carried out in any appropriate mechanical disintegrator such as a jaw crusher or rotary crusher, or hammermill or the like.

Regarding the powdered material added to expedite crystallization and cooling of the partially pyrolyzed reaction product to make the feedstock for the solid state heating stage of the process, other powdered or comminuted materials can be used as the additive if they do not substantially lower the melting point of the reaction mass during the solid state pyrolyzation and provided they are advantageous or at least not deleterious to the end of the final reaction product, such as for animal feed or the like. In the case of the end use being animal feed, for example, advantageous additives may be calcium carbonate or calcium phosphate or other known animal feed additive.

However, the powdered or comminuted additive introduced to the partially pyrolyzed reaction product in making up the feedstock is preferably feed grade biuret such as readily available by-product fines from earlier sizing processing, and offers the advantage of increasing the melting point of the reaction mass during the solid state pyrolyzation (since the proportion of biuret and its homologs is thereby increased in the mass) which in turn permits it being heated during the solid state pyrolyzation to a somewhat higher temperature without melting, thus accelerating the heat conversion.

We have found that the two stage pyrolyzation technique described results in a product which when comminuted needs no further processing before use as animal feed grade biuret. In general, the initial stage of the reaction process is carried out at a temperature above the melting point of urea, forming a partially pyrolyzed reaction product comprising urea, cyanuric acid and biuret. The second stage of the process involves the continued pyrolyzation of the reaction product in particulate, essentially solid state, with forced hot air flow interstitially through the particles, the net effect of which is to reduce the urea content and enhance the biuret content of the reaction mass, while only slightly increasing the cyanuric acid, triuret and other by-product content. During the solid state heat treatment, some urea is sublimed as may also be a slight amount of biuret and possibly others. The effect of this sublimation in reducing the urea content of the product is substantial and is an improtant part of the process when one is attempting to produce FDA acceptable material having not more than 15% urea.

In practicing the present invention, the pyrolysis of urea to give the desired feedstock is accomplished by heating urea above its melting point (132.6° C.) but not over about 165° C. and at an absolute pressure of between 16.5 psia to about 24.5 psia while simultaneously blowing air through the molten urea mass at the rate of from about 2 to about 10 cubic feet of air/hour/pound of molten urea.

The progress of the pyrolysis may be followed by monitoring the disappearance of urea in the melt as well as by the liberation of byproduct ammonia.

In carrying out this invention the raw material urea may be charged to the reactor in either liquid form or in the solid form as urea crystals or urea prills of commerce. When the solid form is charged to a reactor the reactor functions as a melter during the melt up stage and the temperature remains close to the melting point until all of the solid urea has melted. It is usually desirable to have some air sparging through the charge during the meltup stage in order to prevent any urea from fouling or plugging up the air sparger. The air sparger is suitably simply a tube which carries the air from a pressurized air supply to its point of release at or near the bottom of the reactor, well beneath the surface of the urea mass. When urea crystals or prills are charged to a combined melter/reactor due account should be taken of the fact that the bulk density of the solid urea is about 50#/cu.ft., whereas the density of the molten urea is about 80#/cu.ft. In other words, a reactor charged full of urea prills will be only approximately half full when melted down. A practical method of fully utilizing the working capacity of a melter/reactor is to repeatedly add urea either as liquid or prills to the reactor as the original charge of solid urea melts down. The temperature of the air sparged urea pyrolysis may vary between about 145° C. and about 165° C. with the preferred temperature range between about 155° C. to 165° C. Heat may be supplied to melt the urea and to initiate the biuret producing reaction by heat transfer through the walls of the melter/reactor. Conventional heat transfer systems such as steam, Dowtherm heat exchange fluid, electrical resistance heating, or the like, may be used. Electrical resistance heating has the advantage of easy thermostatic control and precise control of the end point of the reaction as a function of kilowatt input. A significant amount of energy may be transferred as contained heat in the sparged air as a result of the heat of compression of the air coming from a pressure blower; for instance a 150 horsepower blower producing air under a pressure of 10 psig will raise the temperature of the sparging air from 21° C. to 60° C. when delivering air at the rate of 1680 C.F.M. in the aeration of a charge of 18,000 lbs. of prilled urea in a 2500 gallon reactor. Since the compression heated sparging air comes in contact with virtually all of the individual prills of urea, the heat transfer in the early stage of the heat-up period is markedly improved over compressed air from an air storage tank where the heat of compression has been lost to the surrounding atmosphere. Significant heat may be recovered by taking the hot off-gas existing from one batch reactor operating at 155° C. and using this hot gas to heat up another batch reactor charged with urea prills and starting a melt-up and reaction cycle.

The sparging gas delivery nozzle or nozzles can be directed downwardly or radially of the reaction vessel and can also be oriented to accomplish air-lift stirring, if desired, in a manner known per se. Separate mechanical stirring of a reacting urea batch undergoing air sparging may also be used but is not necessary. The heat transfer through the walls of a reactor is enhanced by the stirring of the molten urea by the sparging air. Where the hot off-gas from one reactor is used to heat up another, cold reactor, any sublimed urea or urea dust in the hot off-gas from one reactor is trapped in the bed of urea prills of the second reactor which acts thereby as a filter medium.

An important function of sparging air through molten urea undergoing reaction to produce biuret according to the following equation:

$$2\ NH_2CONH_2 \rightarrow NH_2CONHCONH_2 + NH_3 \uparrow$$

is that the removal of byproduct $NH_3$ is facilitated. This is in contrast with the practice of Harmon in U.S. Pat. No. 2,145,392 which employs a vacuum to remove the byproduct $NH_3$. Ammonia plus water vapor is by nature a corrosive system and it is necessary to protect the metal parts of any associated blower system. If one attempts to catch the off-gas ammonia in an aqueous trap operating under vacuum with the trap between the reactor and the vacuum source the amount of vacuum attainable is limited by the vapor pressure of the water and ultimately only a dilute ammonia water solution is produced. This severely limits the potentially attainable vacuum. When air sparging is used to hasten the removal of byproduct ammonia in the pyrolysis of urea the blower is never in contact with any ammonia released during the formation of biuret and the air passing through the reactor and containing the byproduct ammonia may be trapped in an aqueous trap without any corrosion of the blower parts.

An important part of this invention is the recovery of byproduct ammonia as aqueous ammonia, also known in the trade as aqua ammonia, for use as agricultural fertilizer. This is accomplished by sparging air at a rate of from about 2 to about 10 cubic feet (measured at standard temperature and pressure) per hour per lb. of urea undergoing pyrolysis, and passing the hot off-gas containing sublimed urea and sublimed biuret through a water solution of ammonia in equilibrium with the ammonia in the off-gas and containing urea, biuret, and other pyrolysis reaction products in solution whereby any sublimed urea and biuret or any urea dust is trapped in the solution but the gaseous ammonia is not. In practice this urea and biuret particulate and sublimate scrubbing should proceed with the aqueous solution at a temperature corresponding to the wet bulb temperatures of the hot off-gas. The cooled and scrubbed gas existing from the scrubber is then admitted to the bottom of a counter-current absorber column in which water entering at the top of the absorber column is the makeup for the liquid phase. A relatively concentrated aqueous ammonia phase exits from the bottom of the absorber column. The counter-current absorber column has sufficient equivalent absorber plates to remove the ammonia in the gas stream to the desired degree.

DESCRIPTION OF THE PREFERRED EMBODIMENTS

Example I 600 pounds of urea prills were charged into a 100 gallon 316 stainless steel reactor equipped with electrical resistance heaters rated at 36 kilowatts. The 100 gallon reactor was 24" inside diameter in size and had conical heads top and bottom, each having a depth of 3.5". The height of the vertical side between the top and bottom heads was 48". The reactor was equipped with a top-mounted anchor type stirrer operating at 160 RPM. The upper head had one 8" flanged opening, one 4" flanged opening and three 2" flanged openings. The bottom head had one 2" flanged opening in the center which was used to introduce air into the urea mass from below and also to drain the molten product from the reactor. 600 pounds of urea amounts to 53.1 gallons when melted and filled the reactor to a depth of about 2.44' above the bottom drain.

The charge of 600 pounds of urea was melted and heated to a temperature of 152° C. and held at that temperature for a period of 4.5 hours, during which time the evolved ammonia gas was removed by air introduced at 15.82 psia and bubbled through the mass at the rate of 175 cubic feet per minute. The off-gas was run through a water trap. At the end of the 4.5 hour pyrolyzation period, 520 pounds of molten pyrolysis product was recovered at a temperature of 149° C., and upon analysis had the following composition; 33.7% urea, 14.8 cyanuric acid, 46.4% biuret, and 5.1% other homologs, by weight, with a softening point of 128° C.

The molten pyrolysis product was mixed with 60 pounds of feed grade biuret powder analyzing 12% urea, 18.8% cyanuric acid, 63.3% biuret, and 5.9% other homologs, by weight, and then mixed with 123 pounds of powdered material analyzing 34.5% urea, 12.9% cyanuric acid, 47.9% biuret, and 5.5% other homologs, by weight, in order to provide crystallization centers to hasten crystallization, and was then allowed to cool to about 72° C. This composite product was then comminuted to a product having a mesh size between 1 and 4 mesh and used as a feedstock in the oven pyrolyzation process of our patent application Ser. No. 265,550, noting particularly the solid state treatment thereof as set forth in the last portion of Example 5 of said application Ser. No. 265,550. Specifically, as stated in said Example 5, 600 lbs. of the comminuted feedstock material was placed in a 4'×4' steel box with a screen bottom and the box containing this bed of product, with a bed thickness of 11" was placed in a recirculating oven and heated to a temperature of 130° C. by forced air recirculation upwardly through the bed at a rate of 6000 cubic feet per minute. After 24 hours of such recirculation of the heated air, the particles were slightly fused together and were manually broken apart by stirring with a shovel. The heating was then continued by further forced air recirculation at the same temperature for a total period of 40 hours, during which time some 28 lbs. of ammonia and some 22 lbs. of sublimate evolved. The final product, still in discrete particle form with only slight, readily broken surface fusion of the particles, analyzed 14.3% urea, 17.6% cyanuric acid, 62.7% biuret, and 5.4% other homologs, by weight. The aeration rate during this second phase of the process was 17.5 cubic feet/hour/lb. of feedstock. As will be noted, the resultant product has a composition well within the feed grade biuret specification established by the Food and Drug Administration of the U.S. Department of Agriculture and may be used for this purpose without further treatment, except for further comminution of the product, if desired.

Example II

In the following example the reaction was carried out in a 750 gallon reactor made of 316 stainless steel having an internal diameter of 58" and dished heads top and bottom of radius 54". The height between the dished heads was 65". The upper dished head had an 18" manhole, one 10" centrally mounted flanged opening, two 8" flanged openings, and four 3" flanged openings. The bottom dish had one centrally mounted 2" flanged opening and two other 2" flanged openings. An air sparger line made of 5"O.D. pipe projected through one of the 8" flanged openings downward as far as possible and then made a right angle turn to support horizontally a closed end piece of 5" O.D. pipe having six ⅜" dia. holes and fourteen ½" dia. holes in its 56" length. All of the air at 645 C.F.M. was exhausted through these twenty holes and provided intimate contact of the air with the molten urea. The urea was charged through the 18" manhole in the upper head and compressed air at 25.7 psia was introduced through the sparger. The reactor was heated by electric resistance strip heaters attached to the outside shell. Heaters of 135 KW rating were placed on the vertical side wall and heaters of 15 K.W. rating were placed on the bottom dish for a total of 150 K.W. energy input. All of the heaters were thermostatically controlled responsive to a temperature probe immersed in the reaction mass.

An initial charge of 4700 lbs. of urea prills was heated to 148.9° C. in 2 hours 41 minutes while subjected to an airflow of 645 C.F.M. at which time the air flow was stopped and 1184 lbs. additional urea prills were added to give a total charge of 5884 lbs. urea. The temperature dropped to 128.9° C. The airflow was then resumed and continued to the end of the reaction period. 1 hour and 4 minutes after the air flow was resumed, the temperature had risen to 150.5° C. at which time a total of 534 KW hrs of electrical energy had been consumed. The temperature was maintained at 150.5° C. for an additional 2 hours, after which the temperature varied between 150.5° C. and 156.1° C. over a period of an additional 2 hours, at which time the product was removed from the reactor and cooled to a temperature of 37° C. and analyzed using the well known HPLC method. The resulting analysis was: urea 31.3%, cyanuric acid 14.0%, biuret 46.2%, triuret 8.5%, by weight. The heating up time to reaction temperature was 3 hours 44 minutes. The reaction time was 4 hours making the total cycle time 7 hours 44 minutes. This product was eminently suitable for conversion to feed grade biuret according to the procedure set forth in our copending U.S. patent application Ser. No. 265,550. The product was a tan cream color, was substantially odorless, and was easily comminuted into through 1 mesh particle size for the oven treatment to produce feed grade biuret. The air pressure on the reactor was 24.7 psia at the start during the meltup period and then declined to 21.7 psia during the reaction period. With 5884 lbs. of urea prills charged and 645 C.F.M. of air sparged, the aeration rate was 6.58 cu. ft. of air/hour/lb. of urea, producing a product analyzing 31.3% urea.

Example III

A charge of 4800 pounds of urea prills was placed in the 750 gallon reactor described in Example II and heated from 22° C. to 149.4° C. in 3 hours during which time 175 C.F.M. of air was passed thru the molten urea. The temperature of the molten urea was then maintained at about 150° C. for an additional 8.0 hours. The product was then removed from the reactor and cooled.

The product analyzed 44.3% urea and 37.85% biuret, by weight. This shows the effect of aeration at the rate of 2.19 cubic feet of air/hour/lb. of urea on the disappearance of urea and production of biuret when the reaction is carried out at about 150° C. During the run the air pressure in the reactor was 21.7 psia at the start and 20.7 psia at the conclusion. The off gas ammonia was absorbed in water.

In carrying out the invention we have discoverd that the melting point of the crude urea pyrolysis product to be used as the feedstock for biuret producing oven pyrolyzation should preferably be between about 110° C. and about 130° C. and preferably as high as possible to prevent fusion during the oven treatment, since fusion interferes with heat transfer from the hot oven air and the sublimation of urea and byproduct ammonia gas removal. The melting point of the feedstock is affected mostly by the proportionate amounts of urea, biuret, and cyanuric acid. Generally, increased urea content lowers the melting point whereas increased cyanuric acid content raises the melting point and is a function of the phase diagram characteristic of all the urea pyrolysis products. For example, the M.P. of the lowest melting eutectic mixture of urea and biuret is 111.1° C. and has the composition 30% urea and 70% biuret, by weight. For the feedstock of utility in our invention, it is considered that the urea analysis should be not over about 37% and may have any lower value down to about 25%, by weight. The cyanuric acid analysis of a feedstock of utility in our invention may vary from about 3% to 20%, by weight. The triuret analysis may vary from about 3% to 10%, by weight.

Examples IV–IX

The following reaction runs Nos. 4 through 9 were made in the equipment of Example II and following the same experimental procedure as in Example II. The results of the runs are tabulated in the following TABLE ONE together with the published results of the example given in Japan No. 47-41888.

TABLE ONE

| RUN NO. | REACTION TEMP °C. | REACTION TIME IN HOURS | UREA CHARGED TO REACTOR IN LBS. | TOTAL AIR FLOW IN CU. FT. | RATE OF AIR FLOW CU. FT. PER HR. | CU. FT. AIR PER LB. UREA |
|---|---|---|---|---|---|---|
| 4 | 152° C. | 4 | 6160 | 154,800 | 38,700 | 25.1 |
| 5 | 151 | 4.22 | 6300 | 163,314 | 38,700 | 25.9 |
| 6 | 152 | 5.5 | 6800 | 212,850 | 38,700 | 31.3 |
| 7 | 151 | 7.65 | 6000 | 167,535 | 21,900 | 27.9 |
| 8 | 152 | 6 | 5000 | 131,400 | 21,900 | 26.3 |
| 9 | 151 | 9.83 | 7520 | 215,277 | 21,900 | 28.6 |
| JAPAN 47-4188 | 150 | 2 | 0.22 | 93.2 | 46.6 | 423.6 |

| RUN NO. | CU. FT. AIR PER HR PER LB. UREA | ANALYSIS % UREA | ANALYSIS % BIURET | ANALYSIS % CYANURIC ACID | ANALYSIS % TRIURET | POWER USAGE KWHr PER LB. UREA | MELTING POINT OF PRODUCT °C. |
|---|---|---|---|---|---|---|---|
| 4 | 6.28 | 31.1 | 45.1 | 14.2 | 9.6 | 0.1466 | — |
| 5 | 6.14 | 31.8 | 46.8 | 13.1 | 8.3 | 0.1365 | 120 |
| 6 | 5.69 | 32.3 | 45.9 | 15.1 | 6.7 | 0.1326 | 115 |
| 7 | 3.65 | 36.0 | 40.6 | 15.2 | 8.2 | 0.1448 | 122 |
| 8 | 4.38 | 36.2 | 42.5 | 13.0 | 8.3 | 0.1424 | 110 |
| 9 | 2.91 | 37.4 | 41.8 | 16.6 | 4.2 | 0.1360 | 116 |
| JAPAN 47-4188 | 211.8 | 44.0 | 38.8 | 4.0 | 3.8 | — | — |

An important part of our invention is the discovery that the rate of aeration in cubic feet of air/hour/lb. of urea, over a relatively narrow range (2–10 cu.ft/hr/lb. urea) is the major factor in controlling the physical and chemical properties of the feedstock product which render it suitable for solid state pyrolysis to produce feed grade biuret.

As will be readily understood by those skilled in the art, variations and modifications are possible in practice of the present invention. Thus, simply by way of further example, while air has been the primary sparging gas referred to in the foregoing Examples and is believed preferable for practice of the invention because of economic considerations, it is considered technically possible to utilize other gases or mixtures of gases for sparging purposes in the process, so long as the gas or mixture of gases is nonreactive in relation to the pyrolysis reactions. Another example of such a nonreactive gas is nitrogen and also the class of gases known as inert gases.

What is claimed is:

1. The process of preparing animal feed grade biuret, comprising; preparing a feedstock by heating a urea charge at a temperature of between about 145° C. and about 165° C. while simultaneously blowing a nonreactive gas at superatmospheric pressure through the molten urea charge at an aeration rate of from about two to about ten cubic feet of gas/hour/lb. of urea for at least about four hours and until the urea content of the product is reduced to between about 37% and about 25% urea, the cyanuric acid content is between about 3% and about 20% and the melting point of the product is between about 110° C. and about 130° C., by weight; cooling and comminuting the product to form such feedstock; containing the comminuted feedstock as a bed of several inches thickness in a recirculating oven, and passing heated recirculated gas through the bed of feedstock at a temperature slightly below the melting point of the feedstock until the urea content thereof is less than about 15% by weight.

2. The process of claim 1, wherein the temperature at which the urea is heated during gas sparging thereof is from about 155° C. to about 165° C.

3. The process of claim 1, wherein the time of heating and gas sparging is from about 4 hours to about 16 hours.

4. The process of claim 1, wherein the sparging gas is air.

5. The process of claim 1, comprising interrupting the gas sparging and cooling the product when the urea content of the product is reduced to about 30% by weight.

6. The process of preparing animal feed grade biuret, comprising; preparing a feedstock by heating a urea charge at a temperature of between about 145° C. and about 165° C. while simultaneously blowing air at superatmospheric pressure through the molten urea charge at an aeration rate of from about two to about ten cubic feet of gas/hour/lb. of urea for at least about four hours and until the urea content of the product is reduced to between about 37% and about 25% urea, the cyanuric acid content is between about 3% and about 20%, and the melting point of the product is between about 115° C. and about 125° C., by weight; cooling and comminuting the product to form such feedstock; containing the comminuted feedstock as a bed of several inches thickness in a recirculating oven; and passing recirculated air through the bed of feedstock at a temperature slightly below the melting point of the feedstock until the urea content thereof is less than about 15% by weight.

7. The process of claim 6, wherein the time of heating and gas sparging is from about 4 hours to about 16 hours.

8. The process of claim 7, comprising interrupting the gas sparging and cooling the product when the urea content of the product is reduced to about 30% by weight.

* * * * *